(12) United States Patent
Ladebeck et al.

(10) Patent No.: US 7,754,651 B2
(45) Date of Patent: Jul. 13, 2010

(54) CU/ZN/AL CATALYST FOR METHANOL SYNTHESIS

(75) Inventors: Jurgen Ladebeck, Louisville, KY (US); Jurgen Koy, Grosskarolinenfeld (DE); Tiberius Regula, Bad Aibling (DE)

(73) Assignee: Süd-Chemie AG, München (DE)

( * ) Notice: Subject to any disclaimer, the term of this patent is extended or adjusted under 35 U.S.C. 154(b) by 1087 days.

(21) Appl. No.: 10/497,865

(22) PCT Filed: Nov. 6, 2002

(86) PCT No.: PCT/EP02/12395

§ 371 (c)(1), (2), (4) Date: Nov. 3, 2004

(87) PCT Pub. No.: WO03/053569

PCT Pub. Date: Jul. 3, 2003

(65) Prior Publication Data

US 2005/0080148 A1    Apr. 14, 2005

(30) Foreign Application Priority Data

Dec. 8, 2001   (DE) .................. 101 60 486

(51) Int. Cl.
*B01J 23/80* (2006.01)
*B01J 23/72* (2006.01)
*B01J 23/06* (2006.01)

(52) U.S. Cl. .............. 502/342; 502/340; 502/341; 502/343; 502/345; 502/346; 423/592.1; 423/593.1; 423/594.14; 423/600; 423/604; 518/713

(58) Field of Classification Search ......... 502/340–343, 502/345, 346; 518/713, 716; 423/592.1, 423/593.1, 594.14, 600, 604
See application file for complete search history.

(56) References Cited

U.S. PATENT DOCUMENTS

| | | | |
|---|---|---|---|
| 3,850,850 A | 11/1974 | Collins | |
| 3,923,694 A | 12/1975 | Cornthwaite | |
| 4,279,781 A | 7/1981 | Dienes et al. | |
| 4,535,071 A | 8/1985 | Schneider et al. | |
| 4,598,061 A | 7/1986 | Schneider et al. | |
| 5,019,547 A | 5/1991 | Chaumette et al. | |
| 5,254,520 A * | 10/1993 | Sofianos | 502/307 |
| 5,631,302 A | 5/1997 | Konig et al. | |
| 5,990,040 A * | 11/1999 | Hu et al. | 502/342 |

FOREIGN PATENT DOCUMENTS

| | | |
|---|---|---|
| GB | 1286970 | 8/1972 |
| GB | 1366367 | 9/1974 |
| JP | 7008799 | 1/1995 |

* cited by examiner

*Primary Examiner*—Timothy C Vanoy
*Assistant Examiner*—Diana J Liao
(74) *Attorney, Agent, or Firm*—Scott R. Cox

(57) ABSTRACT

Disclosed is an Cu/Zn/Al-catalyst containing copper oxide and zinc oxide as catalytically active components and aluminium oxide as thermostabilising component. The catalyst is characterized in that the Cu/Zn atomic ratio is <2.8 and the aluminium oxide component is obtained from an aluminium hydroxide sol.

4 Claims, No Drawings

CU/ZN/AL CATALYST FOR METHANOL SYNTHESIS

The invention relates to a Cu/Zn/Al-catalyst, containing copper oxide and zinc oxide as catalytically active components and aluminium oxide as thermostabilising component. The invention further relates to a method for manufacturing the catalyst as well as to its use in methanol synthesis.

Cu/Zn/Al catalysts catalysing the transformation of CO, $CO_2$ and $H_2$ to methanol have been known for a long time. However, the atomic ratio of copper to zinc may vary with these known catalysts, wherein copper usually is present in excess. Further, part of the zinc component may be substituted by calcium, magnesium and/or manganese. The aluminium oxide used as thermostabilising component may be substituted in part by chromium oxide. Such catalysts are known, for example, from DE-A 1 965 007, 2 302 658 and 2 056 612 as well as from U.S. Pat. No. 4,279,781. A similar catalyst for methanol synthesis is also known from EP-A-0 125 689. This catalyst is characterized in that a portion of pores having a diameter within a range of 20 to 75 Å is at least 20%, and the portion of pores having a diameter of more than 75 Å is at most 80%. The Cu/Zn-atomic ratio is within a range of 2.8 and 3.8, preferably within 2.8 and 3.2, and the portion of $Al_2O_3$ is 8 to 12 wt.-%.

A similar catalyst for methanol synthesis is known from DE-A-44 16 425. This catalyst has an atomic ratio Cu/Zn of 2:1 and usually consists of 50 to 75 wt.-% CuO, 15 to 35 wt.-% ZnO and further contains 5 to 20 wt.-% $Al_2O_3$.

A similar catalyst is known from JP-A-07008799. This catalyst contains about 10 to 215 parts (atomic ratio) Zn and about 1 to 50 parts Al or Cr per 100 parts Cu.

Finally, a catalyst for synthesis of methanol and alcohol mixtures containing higher alcohols is known from EP-A-0 152 809 containing in the form of an oxidic precursor (a) copper oxide and zinc oxide (b) aluminium oxide as a thermostabilising compound, and (c) at least one alkali carbonate or alkali oxide, wherein the oxidic precursor has a portion of pores having a diameter within 15 and 7.5 nm of 20 to 70% in relation to the total volume, the alkali content is 13 to 130·10$^{-6}$ gram atom alkali metal per gram of the oxidic precursor and wherein the aluminium oxide component has been obtained from a colloidally dispersed aluminium hydroxide (aluminium hydroxide sol or gel).

It has been found, that by decreasing the atomic ratio of Cu/Zn, surprising effects may be obtained as to specific activity and selectivity, in particular at temperatures below 250° C. Further, thermal stability is improved. Therefore, the object of the invention is to provide Cu/Zn/Al-catalysts having a high specific activity, selectivity and thermal stability.

Subject of the invention is a Cu/Zn/Al-catalyst containing copper oxide and zinc oxide as catalytically active components and aluminium oxide as thermostabilising component, characterised in that the Cu/Zn atomic ration is <2.8, preferably within about 1.8 and 2.7, and wherein the aluminium oxide component is at least in part obtained from an aluminium hydroxide sol. The portion of the aluminium oxide component essentially corresponds to the portion in known catalysts.

The catalyst according to the invention has an increased activity in methanol synthesis, in particular at temperatures of less than 250° C., as well as an increased thermal stability in comparison to the catalyst disclosed in EP-A-125 689, wherein the increase in thermal stability is due to the aluminium hydroxide sol. This suppresses coalescence of the copper crystallites after reduction. Most likely the aluminium oxide particles obtained from the aluminium hydroxide sol during heating form netlike elevations on the surface of the catalyst, between which the CuO crystallites and after reduction the copper crystallites are situated so to speak in an "energy sink".

The zinc oxide also acts to stabilize the catalyst in that it forms part of the netlike $Al_2O_3$ structure on the surface of the catalyst thereby contributing to suppress coalescence of the Cu-crystallites after reduction. Further, the zinc oxide acts as a poison trap by reacting with sulfur compounds contained in the starting material.

Preferred embodiments are mentioned in the depending claims.

In particular the size of the copper crystallites in a reduced state is preferably within about 6 to 7 nm.

The size of the Cu-crystallites has been determined by X-ray-powder-diffraction (XRD). The Cu(111) reflex within a range of −43.3°2Θ has been measured. The half width and the integral intensity of the reflex has been calculated by the pseudo Voigt and the Lorentz-Profile-Function. The size of the Cu crystallites has been calculated from the Scherrer-function based on the calculated half width.

The percentage of the aluminium oxide component is preferably about 1 to 20 wt.-%, especially preferred about 5 to 20 wt.-%.

In an oxidic state the catalyst has a BET-surface of about 90 to 120 m$^2$/g and a pore volume of about 320 to 500 mm$^3$/g, preferably about 320 to 380 mm$^3$/g.

The BET-surface has been measured according to the nitrogen single point method in accordance with DIN 66132. The pore volume has been measured according to the mercury intrusion method in accordance with DIN 66133.

As the aluminium hydroxide sol a product obtainable on the market may be used. However, the aluminium oxide sol may also be obtained in that a small portion of $NH_4OH$ is added to a diluted solution of an aluminium salt, wherein warming is avoided to retard transformation to crystalline aluminium metahydroxide (AlO(OH)). According to a further variant boehmit (γ-AlO(OH)) or pseudoboehmit may be treated with nitric acid and the obtained solution is diluted with formation of the sol. According to a further variant a solution of an alkali aluminate (with addition of a small amount of acid, if necessary) may be diluted, whereby the sol is formed.

The oxidic catalysts are usually reduced as follows. Tablets (10 g) are heated in presence of a reducing gas (98% $N_2$, 2% $H_2$) within a tubular reactor at a heating rate of 1° C./min from room temperature to 240° C. The average reduction ratio of Cu is more than 95%.

A further subject of the invention is a method for manufacturing the catalyst mentioned above, characterised in that from a solution of Cu and Zn salts and a part of the Al salts the corresponding hydroxocarbonates or hydroxides are precipitated by addition of an alkali carbonate or alkali aluminate solution, wherein either the solution of the Cu- and Zn-salts or the alkali carbonate or alkali nitrate solution contains an aluminium hydroxide sol, whereupon the obtained precipitate is separated from the precipitation solution, washed, dried, calcined and optionally reduced.

Preferably the corresponding nitrates are used as the Cu- and Zn-salts and the corresponding sodium compounds are used as alkali carbonates and alkali aluminates, respectively.

The precursor of the catalyst according to the invention obtained after precipitation and drying has a smaller ratio of a hydrotalcite analogous phase when compared to the known catalyst because of the aluminium hydroxide sol does no longer react with formation of hydrotalcites. A hydrotalcite analogous phase is understood to be a hydrotalcites in which the magnesium is substituted by copper and zinc. Accordingly, the ratio of the malachite phase in the dried precursor is higher compared to the known catalyst. The malachite phase essentially consists of an alkaline Cu/Zn-carbonate. During thermal treatment a mixed Cu/Zn oxide or a mixture of CuO and ZnO in fine dispersion is formed from that. The hydrotalcite analogous phase forms a Cu/Zn-oxide phase during thermal treatment which effects after reduction a catalyst having a comparatively high stability but low activity. The catalyst obtained from the malachite phase is active but not so stable.

The hydrotalcite analogous phase and the malachite phase may be determined by X-ray diffraction of the dried precursor. After thermal treatment those phases disappear.

The BET-surface is also related to the Cu/Zn atomic ratio. Usually it is located between about 90 and 120 $m^2/g$ and therefore is higher than the BET-surface of known catalysts. Also the pore volume is related to the Cu/Zn atomic ratio. Usually it is located between about 320 and 500 $mm^3/g$, preferably between about 320 to 380 $mm^3/g$ and therefore is higher than for the known catalyst.

A further subject of the invention is in the use of the catalyst in methanol synthesis.

Experiments done with methanol synthesis have shown that with decreasing Cu/Zn atomic ratio the thermal stability of the catalysts is increased. The zinc oxide acts as a substitute avoiding rapid coalescence of the Cu-crystallites in the reduced catalyst. The size of the copper crystallites increases during methanol synthesis depending on the $CO_2$ partial pressure, i.e. the Cu-crystallites grow faster at higher $CO_2$ partial pressures.

In the following the invention is explained with reference to the examples wherein the invention should not be restricted in its scope.

EXAMPLE 1

Cu/Zn=2.3

A) Preparation of the Precipitation Solutions a) Preparation or the Soda Solution A 15.37 wt.-% soda solution having a solution volume of 143 liters was prepared with distilled water (141 liters) by addition of $Na_2CO_3$ (25.15 kg) at 50° C. The solution had a density of 1.154 g/ml at 38° C.

b) Preparation of the Cu/Zn Nitrate Solution:

To $Cu(NO_3)_2 \times 3H_2O$ (20.23 kg) was added distilled water (24.2 kg) of 50° C. in a 50-litre-vessel. Then ZnO-powder (4.43 kg, dispersed in 6.3 kg $H_2O$) was dissolved completely with 86% $HNO_3$-solution in a 30-litre-vessel. The Cu and Zn-solutions were mixed with each other in a 300-litre-vessel. A clear solution without precipitate was obtained.

c) Preparation of the Al/Na Nitrate Solution:

In a 30-litre-vessel was added $NaAlO_2$ (1.63 kg) to distilled water (7.5 kg) at 22° C. Then 68% $HNO_3$ (6.4 kg) was added. During the first 1 to 2 min. after addition of $HNO_3$ gelation and an increase in viscosity was observed. Further, the temperature increased to 97° to 98° C. After addition of $HNO_3$ the solution was coloured slightly brownish but did not contain any precipitate. Then the Al/Na-nitrate solution was pumped into the Cu/Zn-nitrate solution.

d) Preparation of the Aluminium Hydroxide Sol:

Sodium aluminate (1.63 kg) and distilled water (7.5 kg) were stirred for 30 min in a 15-litre-vessel and an aluminium hydroxide sol was formed. The obtained sol (8.46 litre) was pumped into the Cu/Zn/Al-nitrate-solution. A white precipitate formed, which slowly dissolved again.

For completion of the Cu/Zn/Al-solution distilled water was added up to a total volume of 84.6 litre and the solution was heated to 74° C. The density of the solution was 1.350 to 1.352 g/ml.

B) Precipitation

The nitrate solution (containing aluminium hydroxide sol) and the soda solution were pumped at the same time at a temperature of 74° C. through a mixing tube into the precipitation vessel. The temperature in the precipitation vessel was 60° C., the pH was about 6.5. The resting time in the precipitation vessel was adjusted to about 5 to 10 min. The suspension is continuously pumped from the precipitation vessel into the aging vessel.

C) Ageing

After finish of the precipitation the suspension was heated to 70° C. The precipitate was aged for 60 min at 70° C. The colour of the precipitate changed from light blue (beginning of the ageing) to green (end of ageing). The pH-value increased from 6.6±0.1 to 7.3±0.1 during ageing.

D) Washing, Filtration:

The suspension was filtered after ageing. The moist filter cake was dispersed in distilled water and again filtered. This procedure was repeated until the Na-content of the filter cake was <350 ppm.

E) Drying:

The filter cake was dispersed by addition of water to an oxide concentration of 10% and dried in a spray drier at a temperature at the entrance of 275 to 280° C. and a temperature at the exit of 105 to 115° C.

F) Thermal Treatment:

The washed catalyst precursor was then calcined for 3 hours at 320° C.

G) Reduction

The oxidic catalyst precursor was heated in a tube reactor in presence of a reducing gas (98% $N_2$, 2% $H_2$) at a heating rate of 1° C./min from room temperature to 240° C. The average reduction ratio of Cu was 85%. The size of the Cu-crystallites after reduction was 6.3 nm.

EXAMPLE 2

Cu/Zn=2.4

Example 1 was repeated with the difference that the ratio Cu/Zn was adjusted to 2.4 and the pH during precipitation was 7.0±0.1. The size of the Cu-crystallites after reduction was 6.8 nm.

EXAMPLE 3

Cu/Zn=2.62

Example 2 was repeated with the difference that the ratio Cu/Zn was adjusted to 2.62. The size of the Cu-crystallites after reduction was 7.5 nm.

EXAMPLE 4

Cu/Zn=2.8

Preparation of the catalyst according to EP-A-125 689 (comparison example).

For precipitation of the catalyst precursor 2 solutions were prepared:

Solution 1: 418 g copper nitrate and 50 g ZnO were dissolved in 1 litre of water and 148 g $HNO_3$ (52.5%) and then a solution of 93.8 g $Al(NO_3)_3 \times 9\ H_2O$ in 0.5 litre water were added.

Solution 2: 410 g sodium carbonate were dissolved in 2 litre of water.

The solutions were separately heated to 68° C. and combined with vigorous stirring such that the pH-value during precipitation was 6.7. The precipitate was aged at 68° C. in the mother liquor for one hour. Then it was filtered and washed with water until free of sodium. The filter cake was dried at 120° C. and then calcined for 8 hours at 280° C. The calcined product was crushed and then pressed after addition of 2 wt.-% graphite.

The size of the Cu-crystallites after reduction was 8.5 nm.

The chemical composition and the physical properties of the catalysts according to the above examples are summarized in table I.

TABLE I chemical and physical properties

|  | Example 1 | Example 2 | Example 3 | Example 4 |
|---|---|---|---|---|
| chemical composition* |  |  |  |  |
| CuO [%] | 63 | 63 | 64 | 65 |
| ZnO [%] | 27 | 26 | 25 | 24 |
| $Al_2O_3$ [%] | 10 | 11 | 11 | 11 |
| Cu/Zn [mol/mol] | 2.3 | 2.4 | 2.62 | 2.8 |
| physical properties |  |  |  |  |
| tablet size [mm] | 6 · 3.5 | 6 · 3.5 | 6 · 3.5 | 6 · 3.5 |
| powder density [g/l] | 1040 | 1010 | 1050 | 1050 |
| lateral crush strength [N] | 155 | 155 | 160 |  |
| BET [$m^2/g$]** | 98 | 95 | 90 | 80 |
| pore volume [$mm^3/g$]*** | 330 | 330 | 320 | 280 |
| pore volume distribution [%]*** |  |  |  |  |
| >1750 nm | 0 | 0 | 0 | 0 |
| 80-1750 nm | 1.6 | 2.6 | 4.0 | 5.3 |
| 14-80 nm | 65.3 | 66.1 | 60.9 | 71.4 |
| 7.5-14 nm | 33.1 | 31.3 | 35.1 | 23.3 |

*ignition loss determined at 600° C.
**the BET-surface was determined according to the $N_2$-single point method at 77 K in accordance with DIN 66132.
***the pore volume was determined according to the mercury intrusion method in accordance with DIN 66133.

The activities in methanol synthesis were tested under conditions given in table II. The ratio of side products is a measure for selectivity. The results are also included in table II.

TABLE II

Results of methanol synthesis tests

|  | Ex. 1 | Ex. 2 | Ex. 3 | Ex. 1 | Ex. 2 | Ex. 3 |
|---|---|---|---|---|---|---|
| test conditions |  |  |  |  |  |  |
| catalyst volume [ml] | 15 |  |  | 15 |  |  |
| test duration [h] | 245 |  |  | 96 |  |  |
| temperature [° C.] | 250 230 210 250 |  |  | 235 |  |  |
| pressure [bar g] | 60 |  |  | 45 |  |  |
| gas composition [%] |  |  |  |  |  |  |
| $N_2$ |  | 6.88 |  |  | 2.8 |  |
| CO |  | 5.93 |  |  | 10.8 |  |
| $CH_4$ |  | 19.34 |  |  | 7.2 |  |
| $CO_2$ |  | 8.05 |  |  | 3.9 |  |
| $H_2$ |  | 59.79 |  |  | 75.3 |  |
| gas flow [Nl/h] |  | 330 |  |  | 300 |  |
| test results WTY (weight-time-yield) [kg/kg h] |  |  |  |  |  |  |
| T = 250° C. | 1.127 | 1.084 | 1.053 |  |  |  |
| T = 230° C. | 0.946 | 0.75 | 0.739 |  |  |  |
| T = 210° C. | 0.4 | 0.305 | 0.297 |  |  |  |
| T = 250° C. | 1.144 | 1.064 | 1.039 |  |  |  |
| T = 235° C. |  |  |  | 1.28 | 1.206 | 0.959 |
| side products [ppm] total |  |  |  |  |  |  |
| T = 250° C. | 926 | 957 | 1067 |  |  |  |
| T = 230° C. | 568 | 542 | 656 |  |  |  |
| T = 210° C. | 278 | 294 | 336 |  |  |  |
| T = 250° C. | 869 | 967 | 1015 |  |  |  |
| T = 235° C. |  |  |  | 713 | 838 | 1034 |
| ethanol |  |  |  |  |  |  |
| T = 250° C. | 162 | 182 | 245 |  |  |  |
| T = 230° C. | 35 | 45 | 65 |  |  |  |
| T = 210° C. | 2 | 3 | 5 |  |  |  |
| T = 250° C. | 157 | 192 | 243 |  |  |  |

From table II further can be seen that with decreasing Cu/Zn ratio the catalytic activity increases. The long time activity of the catalyst according to the invention is better than the comparative catalyst.

Further, for determining selectivity the side products and the ethanol content were measured as a function of duration of the experiment. The side products are higher hydrocarbons ($C_3$ to $C_{10}$), alcohols ($C_2$ to $C_5$), ethers, esters and ketones. Those were determined by gas chromatography. The side products are disturbing also in the ppm range when present in the methanol. Side products require an expensive processing (distillation) of the methanol.

The results are also presented in table II.

Further, the size of the Cu-crystallites of the catalysts according to examples 1 to 4 before and after methanol synthesis were determined. The results are summarized in table III.

With decreasing Cu/Zn atomic ratio less growth of the Cu-crystallites was observed.

TABLE III

Size of Cu-crystallites before and after methanol synthesis

| catalyst | Cu/Zn atomic ratio | Cu crystallite size [nm] | |
|---|---|---|---|
| | | before test | after test |
| example 1 | 2.3 | 6.3 | 7.5 |
| example 2 | 2.4 | 6.8 | 8.5 |
| example 3 | 2.62 | 7.5 | 10.5 |
| example 4 | 2.8 | 8.5 | 12 |

The invention claimed is:

1. A Cu/Zn/Al-catalyst, comprising copper oxide and zinc oxide as catalytically active components and aluminum oxide as a thermostabilising component, wherein the Cu/Zn atomic ratio is between 2.3 and 2.7, the catalyst in its oxidized form has a BET-surface area of 90 to 120 m$^2$/g and a pore volume of 320 to 380 mm$^3$/g, and the aluminum oxide component is at least in part obtained from an aluminum-hydroxide sol wherein said catalyst is utilized for methanol synthesis with reduced side products in the form of higher hydrocarbons ($C_3$ to $C_{10}$), alcohols ($C_2$ to $C_5$), ethers, esters and ketones.

2. The catalyst of claim 1 in the form of tablets, rings or honeycombs.

3. The catalyst of claim 1, wherein the aluminum oxide component comprises about 1 to 20 weight percent of the catalyst.

4. The catalyst of claim 1, wherein the aluminum oxide component comprises about 5 to 20 weight percent of the catalyst.

* * * * *